United States Patent [19]

Salo

[11] Patent Number: 4,674,518
[45] Date of Patent: Jun. 23, 1987

[54] METHOD AND APPARATUS FOR MEASURING VENTRICULAR VOLUME

[75] Inventor: Rodney W. Salo, Fridley, Minn.

[73] Assignee: Cardiac Pacemakers, Inc., St. Paul, Minn.

[21] Appl. No.: 773,048

[22] Filed: Sep. 6, 1985

[51] Int. Cl.$^4$ .............................................. A61B 5/04
[52] U.S. Cl. .................................... 128/695; 128/713; 128/734; 128/419 PG; 128/419 D; 128/786
[58] Field of Search ............ 128/419 PG, 419 D, 668, 128/687, 693, 694, 695, 700, 713, 734, 784, 786

[56] References Cited

U.S. PATENT DOCUMENTS

| | | | |
|---|---|---|---|
| 3,131,689 | 5/1964 | Rodler | 128/734 |
| 3,320,946 | 5/1967 | Dethloff et al. | 128/734 |
| 3,851,641 | 12/1974 | Toole et al. | 128/734 |
| 3,949,736 | 4/1976 | Vrana et al. | 128/734 |
| 4,291,699 | 9/1981 | Geddes et al. | 128/419 D |
| 4,303,075 | 12/1981 | Heilman et al. | 128/419 PG |
| 4,458,694 | 7/1984 | Sollish et al. | 128/734 |
| 4,587,975 | 5/1986 | Salo et al. | 128/693 |

*Primary Examiner*—William E. Kamm

*Attorney, Agent, or Firm*—Orrin M. Haugen; Thomas J. Nikolai

[57] ABSTRACT

A method and apparatus for the instantaneous measurement of venticular volume using an intracavity electrical impedance catheter having plural pairs of spaced surface electrodes driven by a corresponding plurality of electrical signals, each of the signals exhibiting a different discrete frequency, and having plural pairs of spaced surface electrodes for sensing the potentials at predetermined locations within the ventricle. Switching means are provided for selectively coupling the drive signals to predetermined pairs of surface electrodes and for selecting the sensing electrode pairs to be utilized at any given time for read-back of the sensed potentials. The read-back signals are demodulated and converted from an analog signal to a digital quantity. Then, a digital computer is used to determine from the sensed digital quantities the extrapolated value of impedance corresponding to sources spaced an infinite distance apart. Knowing the extrapolated impedance value, the volume of blood in the ventricle can be computed using the formula $V = \rho L^2 / R_0$ wherein $R_0$ is the extrapolated impedance value, $L$ is the distance between the spaced sensing electrodes spanning the ventricle and $\rho$ is the resistivity of the blood.

11 Claims, 4 Drawing Figures

METHOD AND APPARATUS FOR MEASURING VENTRICULAR VOLUME

BACKGROUND OF THE INVENTION

I. Field of the Invention

This invention relates generally to cardiac monitoring apparatus, and more particularly to a method and apparatus for quantitatively measuring the instantaneous volume of blood contained within a given chamber of the heart whereby stroke volume and cardiac output can be continuously monitored.

II. Discussion of the Prior Art

As is pointed out in my copending application, Ser. No. 362,903, filed Mar. 29, 1982 and entitled: "BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND", the technique of electrical impedance measurement of intravascular volume has been under investigation for over 30 years, but has only recently been applied to the determination of intracardiac volume in humans. In 1953, Rushmer et al in a paper entitled "Intracardiac Plethysmography" (Am. J. Physiol. 174; 171; 1953) discussed an experiment in which electrodes were attached to the walls of both the right and left ventricles of dogs and used to record changes in impedance during contraction. Geddes et al, in a paper entitled "Continuous Measurement of Ventricular Stroke Volume By Electrical Impedance", published in Cardiac Research Center Bulletin, vol. 4, pg. 118 (1966), describes an experiment in which electrodes were sutured to the epicardium of a dog for measuring impedance at 80 kHz during the injection and withdrawal of blood from the animal's with valves sutured closed in vitro. More recently, Baan et al used an 8-ring catheter and a drive frequency of 20 kHz and recorded in dogs a high degree of correlation between left ventricular impedance measurements and stroke volume, the latter being determined simultaneously through the use of an electromagnetic flow meter (Baan et al, "Continuous Stroke Volume and Cardiac Output from Intraventricular Dimensions Obtained With An Impedance Catheter", CardiovasC Res 15; 328; 1981). In a later paper by Baan et al, entitled "Continuous Registration of Relative Left Ventricle Volume in Man" (Circulation 66) (Suppl. II): II-277, 1982, a report is provided on an experiment in which a catheter has been used to continuously record ventricular impedance and relate it to volume in six patients. The first of the aforereferenced Baan et al publications sets out a theoritical basis for the volume determinations based upon impedance measurements.

As a first approximation, the volume of blood that is measured between any two sensing electrodes can be considered to be a cylinder with boundaries defined by the endothelial surfaces of the cardiac walls and by the equally potential surfaces through the electrodes. The total volume of blood within the left ventricular cavity can thus be considered to be a column of the cylinders stacked together. The change in impedance sensed during ventricular contraction in any one of these cylinders is caused by a change in resistance between the two sensing electrodes as a result of a change in the cross-sectional area of the cylinder. The relationship between resistance and cross-sectional area is given by the formula $$R = \rho L / A$$

where R equal resistance, $\rho$ equals resistivity of blood, L equals the distance between sensing electrodes and A equals the cross-sectional area. For a cylindrical volume where volume (V) is equal to cross-sectional area times length (A×L), the above equation may be substituted for resistance $$R = \rho L^2 / V$$

Resistance at end-diastole and end-systole can thus be defined as $$R_{ed} = \rho L^2 / V_{ed} \text{ and } R_{es} = \rho L^2 / V_{es}$$

where "ed" indicates end-diastole and "es" indicates end-systole. By combining these two equations and subtracting the following formula for stroke volume results:

$$V_{ed} - V_{es} = \rho L^2 \left( \frac{R_{es} - R_{ed}}{R_{es} R_{ed}} \right)$$

Thus, for a given cylindrical segment of blood between any two longitudinally spaced sensing electrodes, the change in volume that occurs with ventricular contraction can be determined from the difference in impedance at end-systole and end-diastole. Moreover, since each cylinder of blood within the left ventricle can be thought of as a resistor in series between the driving electrodes, volume measurements for individual cylinders can be added to determine the stroke volume of the whole ventricle.

The theory of impedance volume measurement just presented must be considered an over-simplification since factors critical to accurate measurement have not been addressed. One of the major difficulties encountered with impedance determination of absolute volumes has been in factoring out the contribution of myocardial tissue to measurements of intracardiac electrical impedance. The impedance method of determining ventricular cavity volumes depends on the higher electrical resistivity of myocardial tissue than blood. As a result, the measuring current is primarily contained within the ventricular chamber, and impedance changes should predominantly reflect the time varying quantity of intracavitary blood. Under ideal conditions, if the tissues were a perfect insulator, all of the measuring current would pass only through the ventricular cavity and extremely accurate volume measurements could be made. Support for this concept is derived from impedance measurements of blood volumes contained within a rubber bulb in which correlations of impedance with absolute volumes have been found to be 0.99.

We have determined that the effect of the parallel resistance of the myocardium and surrounding tissue is to decrease the measured resistance and thus add an apparent volume ($V_{OFFSET}$) to the actual ventricular volume.

In addition to the above-described contribution of myocardial impedance to impedance volume measurements, there are other problems in the determination of absolute chamber volumes. One such problem concerns the resistivity of blood, which is not constant, and it has been shown to vary with temperature, hematocrit, and blood velocity. Moreover, it is possible that changes in electrolyte concentrations alter resistivity as well.

When a catheter is positioned within a ventricular chamber and a drive potential of a predetermined frequency is applied between a pair of spaced electrodes, where one is proximate the apex of the chamber and the other is proximate the aortic valve, it is found that the electric field lines are not straight, but are outwardly bowed. Similarly, the equipotential lines are not straight but are also bowed so as to intersect the electric field lines at right angles. This pattern also results in a lack of homogeneity in the current density within the ventricular chamber. Because the volume formula $=\rho L^2/R$ only applies to regularly shaped cylindrical volumes, when an attempt is made to apply that formula to the actual conditions prevailing when spaced drive electrodes are energized, error is introduced into the ventricular volume measurement. This error is especially acute in the right ventricle due to its shape. The extent of the error can be reduced somewhat by effectively breaking up the volume spanned by the drive electrodes into discrete segments, computing the volume of those individual segments and then summing the individual volume measurements to obtain a total volume as in Baan et al. However, this does not address the inappropriate nature of the cylindrical volume formula for this non-cylindrical situation.

SUMMARY OF THE INVENTION

In accordance with the present invention, even greater improvement in the measurement accuracy is achieved by computing a $R_0$ value which is equivalent to what would be measured, assuming that the drive electrodes are spaced an infinite distance apart from one another. When this condition prevails, at least in a mathematical sense, the electric field lines extending between the electrodes becomes straight and parallel as do the equi-potential planes intersecting the field lines at right angles. Knowing the $R_0$ value, then, the formula $V = \rho L^2/R_0$ applies even in the irregularly shaped right ventricle, and it is possible to obtain a more accurate indication of the volume between sense electrode pairs. When the individual segment volumes are summed to provide a total volume figure, the total volume figure is also much more accurate.

The computed volume still includes the $V_{OFFSET}$ due to surrounding tissue but, as in shown in Appendix A hereto, the $V_{OFFSET}$ term has little effect on the computation of stroke volume and thus cardiac output since stroke volume involves only a difference in volumes. In addition, since the ventricular volume measurements are now accurate except for the single additive value, any change in the ventricular volume due to patient condition or therapy may be accurately assessed. For example, a ten ml. decrease in end-diastolic volume measured after infusion of an inotropic drug will be an accurate measurement of the effect of the drug.

To obtain the equivalent $R_0$ value for use in the volume formula, there is provided a catheter having a distal drive electrode positionable proximate the apex of the heart and a proximal drive electrode positionable near the aortic valve. A second pair of spaced-apart drive electrodes is also provided on the catheter, the second pair is being spanned by the first pair. Located between the individual electrodes comprising the second pair are further pairs of sense electrodes. The first and second pairs of drive electrodes are separately energized by constant current sources of differing discrete frequencies. This makes it possible, by appropriate filtering, to isolate the potential contribution at any given sensing electrode pair attributable to each of said first and second sources. By plotting the resistance that is measured as a function of the inverse of the distance from the sense pair to the corresponding drive pair for each frequency component in Cartesian coordinates, a line can be drawn between the two plotted resistance values and, when the line is extended (extrapolated) to the Y-intercept, it corresponds to the impedance where the drive electrodes are an infinite distance apart.

The foregoing may be accomplished by having two different sources, each separately and simultaneously energized at two different frequencies whereby the contribution of each can be isolated using digital filtering techniques. Alternatively, the two pairs of drive electrodes may be alternately energized by the same current source with the resistance measured for each of the two drive configurations stored separately within the device. Once the two resistance values and the distance between the sensed pair to the respective drive pair are known, the foregoing extrapolation can take place to obtain the desired equivalent $R_0$ value. Once $R_0$ is known, the volume can be more accurately calculated than has heretofore been possible.

The method of the present invention permits more accurate stroke volume and cardiac output measurements in patients than has heretofore been possible on a continuous basis. Ventricular volume information can aid in the diagnosis of valvular disease and hypertrophy. It also assists in the determination of the extent and effect of cardiac infarction and ischemia and is also useful in assessing and monitoring drug intervention to control such diseases as congestive heart failure. Such prior art techniques as thermal dilution or indicator dilution can only be used infrequently and are not suitable for long-term monitoring situations. The dual source ventricular impedance plethysmography technique of the present invention allows a clinician to visually observe each ventricular contraction without the injection of any substance into the heart or other type of operator intervention over extended time periods and during physical maneuvers such as exercise. In that the digital-to-analog converter may sample the ventricular volume readings at a rate of 100 Hz, no event with a duration greater than 10 milliseconds would escape the attention of the physician. Thus, not only can long term cardiac output changes be monitored, but the effect of preventricular contractions may be assessed on an individual basis. Because the time rate of change of volume for each beat becomes available using the technique of the present invention, it is also possible to estimate the contractility of the heart. Also, by simultaneously monitoring pressure as well as ventricular volume, stroke work may be calculated and that information may be used in the management of congestive heart failure.

OBJECTS

It is accordingly a principal object of the present invention to provide an improved method of determining the ventricular volume of a heart using an impedance catheter.

Another object of the invention is to provide a method and apparatus for measuring stroke volume and cardiac output with an accuracy greater than has heretofore been possible using known prior art techniques.

A still further object of the invention is to provide a method and apparatus for measuring ventricular volume of an animal heart wherein the effective impedance of the chamber is calculated as if the potential source is at an infinite distance from the sensing electrodes.

Still another object of the invention is to provide a method of applying impedance plethysmography using dual frequency sources or a switched source to more accurately determine the ventricular volume of a heart.

These and other objects and advantages of the invention will become apparent to those skilled in the art from the following detailed description of a preferred embodiment, especially when considered in conjunction with the accompanying drawings.

DESCRIPTION OF THE PREFERRED EMBODIMENT

Figure 1:
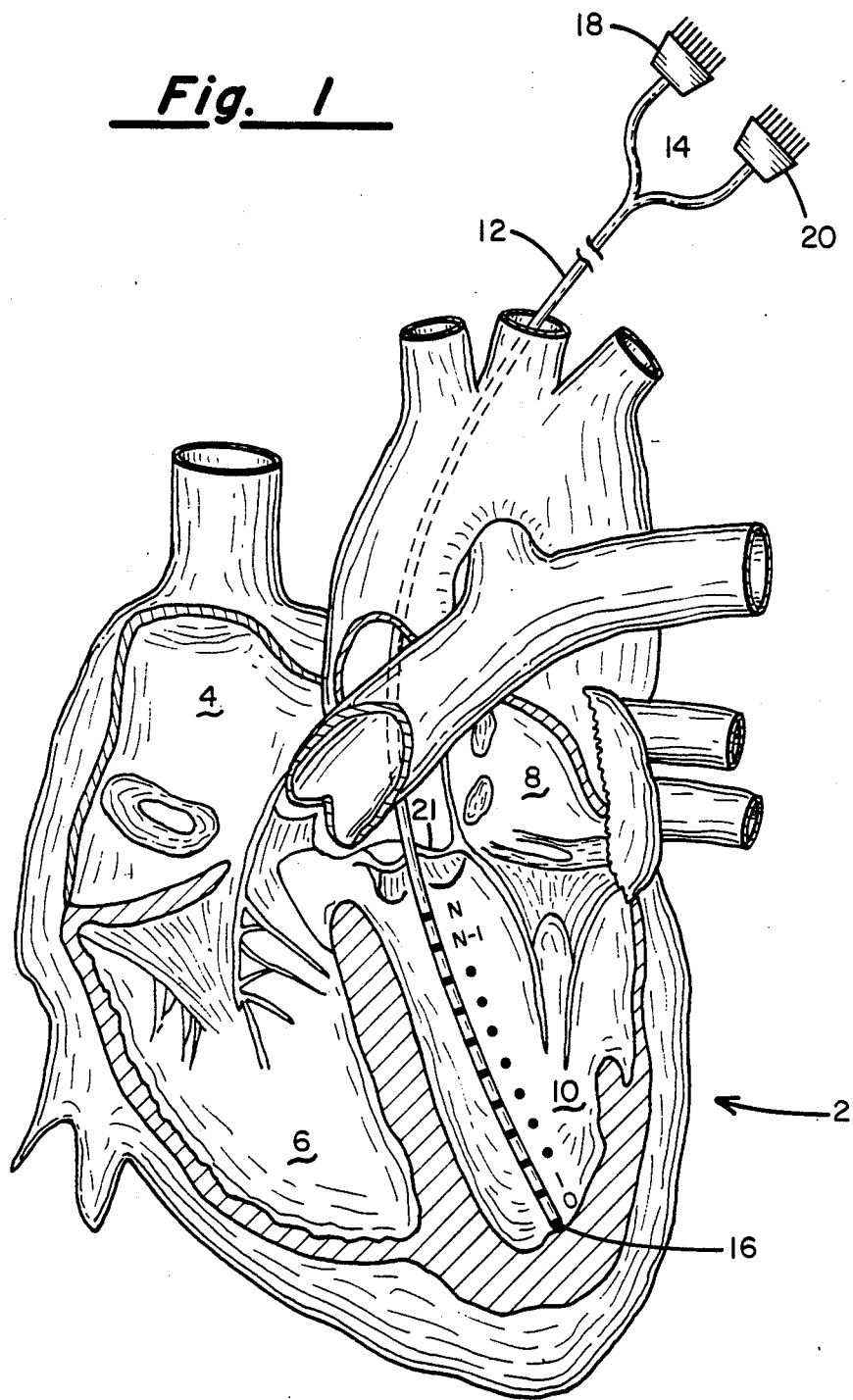
FIG. 1 is a sectional view of the heart showing the impedance catheter disposed in the left ventricle.

Referring to FIG. 1, there is shown in section a human heart 2, the major chambers of which are the right atrium 4, the right ventricle 6, the left atrium 8 and the left ventricle 10. For measuring the stroke volume and total volume of the left ventricle in accordance with the present invention, there is positioned in that chamber an impedance catheter 12 having a proximal end 14 and a distal end 16. The catheter may be made in accordance with the teachings of co-pending application Ser. No. 445,240, filed Nov. 29, 1982, and now U.S. Pat. No. 4,559,951 entitled "CATHETER ASSEMBLY", that application being assigned to the assignee of the present invention. As such, it includes at least one tubular sheath having a plurality of spaced surface electrodes disposed sufficiently near the distal end 16 of the catheter so that those electrodes effectively span the length dimension of the chamber whose volume is to be measured, here the left ventricle. In FIG. 1, the surface electrodes are illustrated as comprising spaced-apart rings labeled 0 through N. Each of the ring electrodes has associated therewith an elongated conductor which, in accordance with the aforereferenced application, may be embedded in the wall of the tubular catheter 12 and extends the entire length thereof, terminating at one or the other of the electrical connectors 18 or 20. The most distal of the surface electrodes is positioned proximate the apex of the left ventricle 10 while the most proximal surface electrode is disposed near the aortic valve 22.

In a practical embodiment of the invention, it was found convenient to provide twelve such surface electrodes, each being spaced from the other by approximately one centimeter. Limitation to these measurements, however, is not intended and, in fact, it is conceived that different catheters having a different number and spacing of ring electrodes may be used when measuring the volume of, say, the right ventricle 6. It is also contemplated that the catheter 12 may have multiple lumens as well as other sensors associated with it for simultaneously monitoring pressures and other parameters while volume measurements are underway. In that the method of the present invention pertains primarily to accurate volume measurement using impedance plethysmography, only those aspects of the catheter relating to such volume measurements will be discussed herein.

Figure 2:
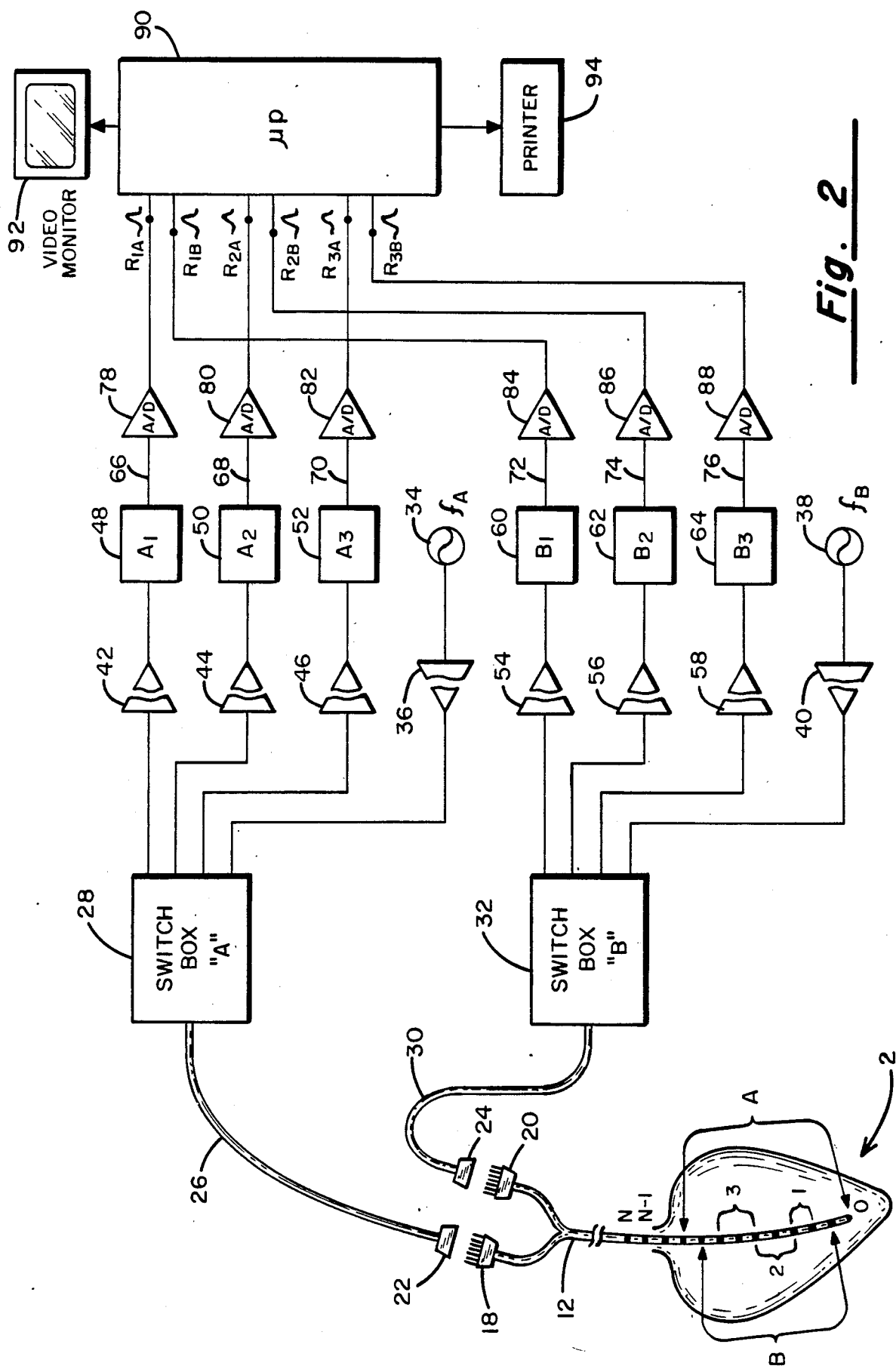
FIG. 2 is a schematic block diagram of the circuitry useful in carrying out the method of the present invention.

Referring next to FIG. 2, there is shown by means of a block diagram the electronic circuitry which may be used in carrying out the method of the present invention. As is shown diagrammatically at the extreme left in FIG. 2, the left ventricle 10 as contains the catheter 12, with that catheter having the spaced ring surface electrodes 0 through N extending proximally from its distal end. The connectors 18 and 20 are arranged to mate with corresponding connector elements 22 and 24. The terminal points in connector half 22 individually connect by conductors in the cable 26 to the switch box "A" identified by numeral 28. Similarly, the connector points in the connector half 24 are individually coupled by conductors in the cables 30 to the switch box "B" identified by numeral 32.

Each of the cables 26 and 30 are wired such that the electrodes 0 through N are connected to the interface with the switch box 28 or 32, respectively. The switch box itself may typically comprise a plurality of multi-positioned rotary switches configured such that any one of the plural inputs may be connected to any of the outputs. Alternatively, other switching devices, such as push-button matrix switches or digitally controlled analog switches may be used in implementing the two switch boxes. Associated with switch box "A" is a first constant current source including an oscillator 34 and an isolation amplifier 36. The output from the isolation amplifier is adapted to be connected through switch box "A" so as to impress the drive signal of frequency "A" between the distal electrode 0 and a surface ring electrode which is located proximal to the chamber to be measured when the distal electrode 0 is located at the apex of that chamber. The bracket labeled "A" at the extreme left in FIG. 2 is intended to indicate that it is the source of frequency $f_A$ that is impressed across the indicated electrodes.

In a like manner, a second constant current source including an oscillator 38 having a frequency $f_B$ different from $f_A$ and an isolation amplifier 40 connects through the switch box "B" 32 and the cable 30 so as to impress the drive signal of a frequency $f_B$ between the surface electrode pair identified by the bracket labeled "B". It will be noted that the spacing between surface electrode pairs "A" is greater than the distance between the surface electrode pairs identified by "B", i.e., pair "A" spans pair "B". Typically, but with no limitation intended, the frequency of oscillator 34 may be 2,600 Hz while the frequency of the oscillator 38 may be 3,600 Hz.

The application of drive "A" via switch box 28 between the distal electrode 0 and the more proximal electrode indicated by the other end of bracket "A" results in the development of corresponding potentials between the sense pairs 1, 2 and 3 spanned by those drive electrodes. Similarly, the application of drive "B" also results in potential signals being developed across the sense pairs 1, 2 and 3. Because the frequency of drive "A" is different from the frequency of drive "B", it is possible to discriminate and thereby determine what the potential contribution due to each discrete drive frequency is.

The output from the switch box "A" 28 is coupled through isolation amplifiers 42, 44 and 46 to amplifier/demodulator circuits 48, 50 and 52. Likewise, switch box "B" 32 provides outputs to isolation amplifiers 54, 56 and 58 and thence to amplifiers/demodulators 60, 62 and 64.

The demodulators 48, 50 and 52 serve to filter and demodulate the input signals from a sense pair, producing an output proportional to the impedance between a pair of sense electrodes. Thus, demodulator 48 labeled "A₁" produces a signal on its output line 66 proportional to the impedance between the sense pair 1 due to drive "A" and likewise demodulators 50 and 52 develop analog signals proportional to the impedance between sense pairs 2 and 3 due to drive "A". In exactly the same fashion, the demodulators 60, 62 and 64 function to produce analog signals on their respective output lines 72, 74 and 76 proportional, respectively, to the impedance between sense pairs 1, 2 and 3 due to the application of drive "B". While in FIG. 2, the demodulation circuitry is represented by a block, those desiring further information on a specific implementation may refer to my aforereferenced co-pending patent application Ser. No. 362,903, filed Mar. 29, 1982.

Each of the aforementioned output lines 66 through 76 feeds into an analog-to-digital converter 78 through 88. Each such A/D converter may comprise a 12-bit converter which samples its associated channel at, for example, a 100 Hz rate and outputs its digitized waveform to a microprocessor system 90. The computer is programmed to generate a single corrected instantaneous impedance for each sense pair from the two impedance values measured at the two drive frequencies and to convert this value into a segment volume for each ring pair by means of the formula $V = \rho L^2 / R_0$ and then summing the volumes from each ring pair to produce the total instantaneous ventricular volume. These computed parameters may be displayed on a video monitor 92 or, when "hard copy" is desired, the data may be recorded by means of a printer/plotter 94.

Figure 3:
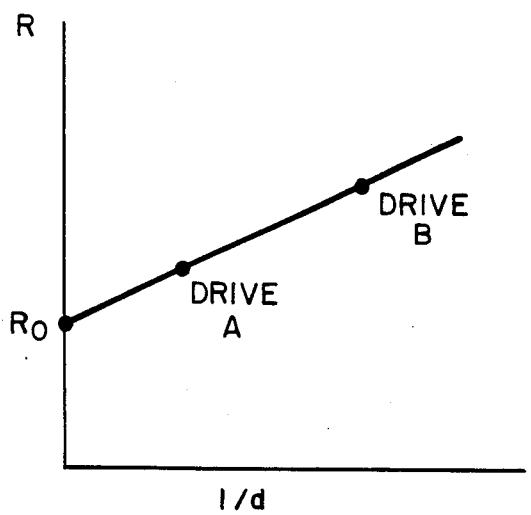
FIG. 3 comprises a plot showing the manner in which the corrected impedance ($R_0$) is obtained.

Referring to FIG. 3, the parameter $R_0$ used in the above formula is obtained by plotting the impedance between a sense electrode pair due to drive "A" and plotting the impedance between that same sense electrode pair due to drive "B" on a set of Cartesian coordinates where the ordinate axis is the inverse of the distance between the drive point and the sense point. When a line is passed through these two points and extended over to the abscissa, its point of intersection corresponds to the impedance value which would theoretically be measured if the driven electrodes were spaced an infinite distance apart. By using this value when computing the volume for the individual segments, significantly improved accuracy of the impedance plethysmography method for determining chamber volume results upon summing each of the segment volumes as compared to the accuracies reported by other researchers. This is especially true in the right ventricle where due to its shape, the impedance technique has not been previously capable of quantitative measurement. Thus, by following the method described herein, it has been possible to develop instrumentation for measuring chamber volume with its offset volume, $V_0$, as well as stroke volume on a real-time basis and with substantially greater accuracy than has been obtainable using prior art techniques, such as thermal dilution, Fick cardiac output and dye dilution.

Figure 4:
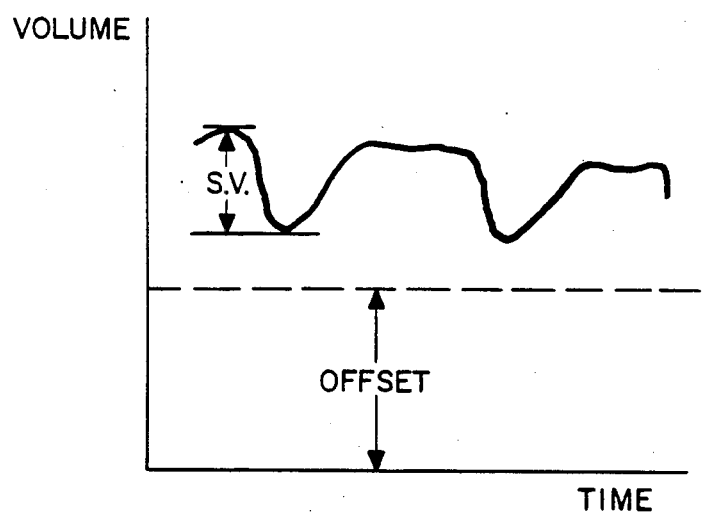
FIG. 4 is a waveform showing the real-time variation in chamber volume with successive heartbeats.

Referring to FIG. 4, there is shown a waveform showing the manner in which the computed chamber volume varies with successive heartbeats. The actual chamber volume is superimposed upon an offset volume, $V_0$, which arises as a result of the parallel resistance of surrounding tissue. The difference in volume between end-diastole and end-systole is the stroke volume. A measure of the offset volume, $V_0$, may be obtained by first computing end-diastolic volume (EDV), end-systolic volume (ESV) and stroke volume (SV) under normal resting conditions. Then, the volume of the heart may be changed by cardiac pacing drugs or other means. Finally, a plot is made of EDV and ESV against SV. Extropolating to a condition of SV=0 gives a measure of $V_0$. Once this $V_0$ has been computed, it may be subtracted from all volume computations to give a more accurate ventricular volume measurement. Thus, not only can the method of the present invention be used to measure the volume of individual segments of the chamber and its total volume but, also, the stroke volume can be computed by merely subtracting the trough reading from the peak reading in FIG. 4.

This invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself.

APPENDIX A

Stroke volume (SV) is defined as follows:

$$SV = EDV - ESV$$

Using the basic cylindrical equation with the measured End Diastolic and End Systolic Resistances (EDR$_{MEAS}$, ESR$_{MEAS}$), $$SV = \rho L^2 / EDR_{MEAS} - \rho L^2 / ESR_{MEAS}$$

But the actual measured resistances at EDV and ESV are a parallel combination of the EDR and ESR due to the blood volume with the tissue resistance $R_{TISS}$.

$$SV = \frac{\rho L^2}{\frac{EDR \cdot R_{TISS}}{R_{TISS} - EDR}} - \frac{\rho L^2}{\frac{ESR \cdot R_{TISS}}{R_{TISS} - ESR}}$$

$$SV = \rho L^2 \frac{ESR(R_{TISS} - EDR) - EDR(R_{TISS} - ESR)}{EDR \cdot ESR \cdot R_{TISS}}$$

$$SV = \rho L^2 \frac{(ESR - EDR) R_{TISS}}{ESR \cdot EDR \cdot R_{TISS}}$$

$$SV = \rho L^2 \frac{ESR - EDR}{ESR \cdot EDR} = \rho L^2 (1/EDR - 1/ESR)$$

$$SV = \rho L^2 / EDR - \rho L^2 / ESR$$

Thus one can use the measured resistances at EDV and ESV and compute the same SV that would be computed if the actual EDR and ESR for the blood volume were known. In other words, the tissue impedance has no effect on the computed stroke volume.

What is claimed is:

1. A method for determining the instantaneous volume of blood in a chamber of an animal heart, comprising the steps of:

(a) inserting an elongated tubular catheter percutaneously into said chamber, said catheter having a plurality of longitudinally-spaced electrodes on the surface thereof which are individually connected to a corresponding plurality of terminals at the proximal end of said catheter by conductors passing through said tubular catheter, the longitudinal spacing being such that the distal electrode and proximal electrode are located at the apex and proximate the entrance to said chamber, respectively;

(b) first driving said distal electrode and proximal electrode as a first pair of driving electrodes with a constant current source;

(c) next driving the penultimate distal electrode and the second most proximal electrode as a second pair of driving electrodes with a constant current source;

(c) selectively and sequentially detecting the potential signal developed between pairs of sensing electrodes located intermediate said second pair of driving electrodes attributable to the application of said driving constant current source to the respective first and second pairs of driving electrodes, said potentials being proportional to the instantaneous impedance of the medium existing between the selected pairs of intermediate sensing electrodes;

(e) converting the detected potential signals to digital quantities;

(f) applying said digital quantities to a programmed digital computing device;

(g) generating a single corrected instantaneous impedance value for each pair of intermediate sensing electrodes from the two impedance values detected due to the application of the constant current source to said respective first and second pairs of driving electrodes;

(h) calculating from said single corrected instantaneous impedance value a segment volume for each pair of sensing electrodes; and (i) summing said segment volumes for each pair of sensing electrodes to produce said total instantaneous ventricular volume.

2. The method as in claim 1 wherein said reopective first and second pairs of driving electrodes are energized simultaneously by separate constant current sources of differing frequencies.

3. The method as in claim 1 wherein said single corrected instantaneous impedance value corresponds to that obtained between two of said intermediate sense electrodes due to said sources being spaced an infinite distance apart.

4. The method as in claim 1 and further including the step of detecting the maximum and minimum excursions of said total instantaneous ventricular volume and determining the stroke volume of said chamber therefrom.

5. A method for determining the instantaneous volume of blood in a chamber of an animal heart, comprising the steps of:

(a) inserting an elongated tubular catheter percutaneously into said chamber, said catheter having a plurality of longitudinally-spaced electrodes on the surface thereof which are individually connected to a corresponding plurality of terminals at the proximal end of said catheter by conductors passing through said tubular catheter, the longitudinal spacing being such that the distal electrode and proximal electrode are located at the apex and proximate the entrance to said chamber, respectively;

(b) driving said distal electrode and proximal electrode with a constant current source of a first frequency;

(c) driving the penultimate distal electrode and the second most proximal electrode with a constant current source of a second frequency different from said first frequency;

(d) selectively and sequentially detecting the potential signal developed between pairs of sensing electrodes located intermediate said penultimate distal electrode and the second most proximal electrode attributable to said constant current source of a first frequency and to said constant current source of a second frequency, said potentials being proportional to the instantaneous impedance of the medium existing between the selected pairs of intermediate sensing electrodes;

(e) converting the detected potential signals to digital quantities;

(f) applying said digital quantities to a programmed digital computing device;

(g) generating a single corrected instantaneous impedance value for each pair of intermediate sensing electrodes from two impedance values corresponding to said first and second frequencies;

(h) calculating from said single corrected instantaneous impedance value a segment volume for each pair of sensing electrodes; and (i) summing said segment volumes for each pair of sensing electrodes to produce said total instantaneous ventricular volume.

6. The method as in claim 5 wherein said single corrected instantaneous impedance value corresponds to that obtained between two of said intermediate sense electrodes due to said sources being spaced an infinite distance apart.

7. The method as in claim 5 and further including the step of detecting the maximum and minimum excursions of said total instantaneous ventricular volume and determining the stroke volume of said chamber therefrom.

8. The method as in claim 1 or 5 and further including the step of multiplying said stroke volume quantity by the animal's heartrate to provide a measured value of cardiac output.

9. Apparatus for measuring the instantaneous volume of blood in a chamber of the heart, comprising in combination:

(a) an elongated tubular intravascular catheter having a proximal end and a distal end with a first pair of drive electrodes attached to the exterior surface thereof and spaced apart from one another by a predetermined distance, $d_1$, which is less than the length dimension of said chamber, a second pair of drive electrodes attached to the exterior surface thereof and spaced apart from one another by a predetermined distance, $d_2$, where $d_2$ is less than $d_1$, said second pair of drive electrodes being spanned by said first pair of drive electrodes and a plurality of pairs of sense electrodes attached to the surface thereof and longitudinally spaced therealong between said second pair of drive electrodes, said first and second pairs of drive electrodes and said plurality of pairs of sense electrodes being electrically coupled, individually, to a terminal at said proximal end of said catheter;

(b) a first constant current source of a frequency, $f_1$;
(c) a second constant current source of a frequency, $f_2$;
(d) switching means joined to said terminals for coupling said first constant current source to said first pair of drive electrodes and for coupling said second constant current source to said second pair of drive electrodes;
(e) signal detector means connectable through said switching means to predetermined pairs of said plurality of pairs of sense electrodes for producing signal waves corresponding to the impedance of the medium present between the sense electrode pair selected by said switching means attributable to said first and second constant current sources;
(f) means operatively coupled to said signal detector means for sampling said signal waves at a predetermined rate and converting said signal waves to digital values representative of impedance values; and
(g) computing means coupled to receive said digital values, said computing means being programmed to extrapolate from said impedance values measured at the drive frequencies $f_1$ and $f_2$ an effective impedance value as if said distances $d_1$ and $d_2$ were infinitely large and computing the volume of the segments between selected pairs of said sense electrodes using the formula $V = \rho L^2/R_0$ where L is the distance between electrodes of said selected pair of sense electrodes, $\rho$ is the resistivity of the medium and $R_0$ is said effective impedance value.

10. Apparatus for measuring the instantaneous volume of blood in a chamber of the heart, comprising in combination:

(a) an elongated tubular intravascular catheter having a proximal end and a distal end with a first pair of drive electrodes attached to the exterior surface thereof and spaced apart from one another by a predetermined distance, $d_1$, which is less than the length dimension of said chamber, a second pair of drive electrodes attached to the exterior surface thereof and spaced apart from one another by a predetermined distance, $d_2$, where $d_2$ is less than $d_1$, said second pair of drive electrodes being spanned by said first pair of drive electrodes and a plurality of pairs of sense electrodes attached to the surface thereof and longitudinally spaced therealong between said second pair of drive electrodes, said first and second pairs of drive electrodes and said plurality of pairs of sense electrodes being electrically coupled, individually, to a terminal at said proximal end of said catheter;
(b) constant current source;
(c) switching means joined to said terminals for coupling said constant current source sequentially to said first pair of drive electrodes and to said second pair of drive electrodes;
(d) signal detector means connectable through said switching means to predetermined pairs of said plurality of pairs of sense electrodes for producing signal waves corresponding to the impedance of the medium present between the sense electrode pair selected by said switching means attributable to said constant current source being coupled to first pair of drive electrodes and to said second pair of drive electrodes;
(e) means operatively coupled to said signal detector means for sampling said signal waves at a predetermined rate and converting said signal waves to digital values representative of impedance values; and
(f) computing means coupled to receive said digital values, said computing means being programmed to extrapolate from said impedance values measured due to said constant current source coupled to said first pair of drive electrodes and to said second pair of drive electrodes and effective impedance value as if said distances $d_1$ and $d_2$ were infinitely large and computing the volume of the segments between selected pairs of said sense electrodes using the formula $V = \rho L^2/R_0$ where L is the distance between electrodes of said selected pair of sense electrodes, $\rho$ is the resistivity of the medium and $R_0$ is the effective impedance value.

11. The apparatus as in claims 9 or 10 wherein said computer is further programmed to sum the individual segment volumes to provide a total instantaneous volume for said chamber.

* * * * *